(12) United States Patent
Stössel et al.

(10) Patent No.: US 9,029,539 B2
(45) Date of Patent: May 12, 2015

(54) METAL COMPLEXES WITH BIPODAL LIGANDS

(75) Inventors: Philipp Stössel, Frankfurt (DE); Anja Gerhard, Veitschöchheim (DE)

(73) Assignee: Merck Patent GmbH (DE)

( * ) Notice: Subject to any disclaimer, the term of this patent is extended or adjusted under 35 U.S.C. 154(b) by 1218 days.

(21) Appl. No.: 10/578,039

(22) PCT Filed: Oct. 21, 2004

(86) PCT No.: PCT/EP2004/011890
§ 371 (c)(1),
(2), (4) Date: May 1, 2006

(87) PCT Pub. No.: WO2005/042550
PCT Pub. Date: May 12, 2005

(65) Prior Publication Data
US 2007/0082284 A1 Apr. 12, 2007

(30) Foreign Application Priority Data
Oct. 30, 2003 (DE) .................. 103 50 722

(51) Int. Cl.
C07F 15/00 (2006.01)
H01L 51/50 (2006.01)
H01L 51/00 (2006.01)
C07D 213/26 (2006.01)
C07D 213/30 (2006.01)
C07F 9/58 (2006.01)

(52) U.S. Cl.
CPC ............ *H01L 51/009* (2013.01); *C07D 213/26* (2013.01); *C07D 213/30* (2013.01); *C07F 9/585* (2013.01); *C07F 9/587* (2013.01); *C07F 15/0033* (2013.01); *C07F 15/0086* (2013.01); *H01L 51/0077* (2013.01); *H01L 51/0083* (2013.01); *H01L 51/0085* (2013.01); *H01L 51/0087* (2013.01); *Y02E 10/549* (2013.01)

(58) Field of Classification Search
USPC ................. 546/2; 428/689, 690; 313/504
See application file for complete search history.

(56) References Cited

U.S. PATENT DOCUMENTS

| 4,539,507 | A | 9/1985 | VanSlyke et al. |
| 5,151,629 | A | 9/1992 | VanSlyke |
| 5,621,131 | A | 4/1997 | Kreuder et al. |
| 6,613,583 | B1 | 9/2003 | Richter et al. |
| 6,653,438 | B1 | 11/2003 | Spreitzer et al. |
| 7,332,232 | B2 | 2/2008 | Ma et al. |
| 2004/0138455 | A1 | 7/2004 | Stossel et al. |

(Continued)

FOREIGN PATENT DOCUMENTS

DE 103 04 819 8/2004
DE 103 17 556 11/2004
DE 103 28 627 2/2005

(Continued)

OTHER PUBLICATIONS

Zhang, Huichang et al., "Synthesis of Binucleating Ligands of Pyridylphenol", Synthetic Communications, 31(8), pp. 1129-1139 (2001).
Hannon, Michael J. et al., "Preparation of Substituted thri(2-pyridyl)methanol derivatives as mimics of the metal binding site of carbonic anhydrase", Tetrahedron Letters 39 (1998), pp. 8509-8512.
Bonnemann, et al., "Cobalt-catalyzed one-step synthesis of dipyridines," *Synthesis*, (1975), No. 9, pp. 600-602. (Cited in Japanese Office Action mailed Sep. 24, 2010. No translation available).
Ho, et al., "Syntheses, structures and electrochemical properties of single and double helical inorganic complexes containing new polypyridine ligands," *J. Chem. Soc., Dalton Trans.*, (1996), pp. 1829-1834.

(Continued)

*Primary Examiner* — Charanjit Aulakh
(74) *Attorney, Agent, or Firm* — Drinker Biddle & Reath LLP

(57) ABSTRACT

The invention relates to a compound of the Structure 1

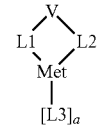

Structure 1 wherein Structure 1 contains a metal Met, coordinated to a tetradentate chelating ligand Lig of Structure 2

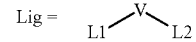

Structure 2 where V is a bridging unit which contains 1 to 40 atoms from the third, fourth, fifth and/or sixth main group and connects the two ligand moieties L1 and L2, which may be identical or different on each occurrence, covalently to one another, and where the two ligand moieties L1 and L2 satisfy Structure 3

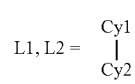

Structure 3 where Cy1 and Cy2, identically or differently on each occurrence, correspond to a substituted or unsubstituted, saturated, unsaturated or aromatic homo- or heterocyclic ring, which is in each case bonded ionically, covalently or coordinatively to the metal via a ring atom or via an atom bonded exocyclically to the homo- or heterocyclic ring; and where L3, identically or differently on each occurrence, is a mono- or bidentate, neutral or monoanionic ligand, and where a is 0, 1 or 2. The present invention describes novel metal complexes with bipolar ligands. Compounds of this type can be employed as functional materials in a number of different applications which can be ascribed to the electronics industry in the broadest sense.

18 Claims, No Drawings

(56) References Cited

U.S. PATENT DOCUMENTS

| | | | |
|---|---|---|---|
| 2006/0063027 A1 | 3/2006 | Vestweber et al. | |
| 2006/0182992 A1 | 8/2006 | Nii et al. | |

FOREIGN PATENT DOCUMENTS

| | | | |
|---|---|---|---|
| DE | 103 37 346 | 3/2005 | |
| EP | 0 707 020 | 4/1996 | |
| EP | 0 842 208 | 5/1998 | |
| EP | 0 894 107 | 2/1999 | |
| EP | 1 028 136 | 8/2000 | |
| JP | 2003-157006 | 1/2004 | |
| JP | 2005-310733 A | 11/2005 | |
| WO | WO-92/18552 | 10/1992 | |
| WO | WO-98/22148 | 5/1998 | |
| WO | WO-00/22026 | 4/2000 | |
| WO | WO-00/70655 | 11/2000 | |
| WO | WO-01/70395 | 9/2001 | |
| WO | WO-02/068435 | 9/2002 | |
| WO | WO-2004/041901 | 5/2004 | |
| WO | WO-2004/058911 | 7/2004 | |
| WO | WO 2004/108856 | 12/2004 | |
| WO | WO 2004/108857 A1 * | 12/2004 | ............. C09K 11/06 |
| WO | WO-2004/108875 A1 | 12/2004 | |

OTHER PUBLICATIONS

Lhoták, et al., "Preparation of New Organic Luminophores Based on 3,5-Diacetylpyridines," *Collect. Czech. Chem. Commun.* (1992), vol. 52, pp. 1937-1946.

Fritsky, et al., "Allosteric Regulation of Artificial Phosphoesterase Activity by Metal Ions," *Angew. Chem, Int. Ed.*, (2009), vol. 39, No. 18, pp. 3255-3258.

Tang, et al., "Synthesis and crystal structures of Group 6 metal carbonyl complexes containing S-rich bis(pyrazol-1-yl)methane ligands," *Journal of Organometallic Chemistry*, (2002), vol. 649, pp. 152-160.

Alonso, et al., "Cyclometallated compounds of Pd(II) with pyrazole derivatives, Unusual double paddadatikon of diarylbis(N-pyrazolyl)methanes," *Journal of Organometallic Chemistry*, (1994), vol. 484, pp. 19-26.

Kashima, et al., "Asymmetric Diels Alder Reaction using Pyrazole Derivatives as a Chiral Catalyst," *Journal of Heterocyclic Chemistry*, (2003), vol. 40, No. 4, pp. 681-688.

European Search Report dated Aug. 17, 2011, in European Application No. 04790697.9.

Bodar-Houillon, F., et al., "Synthesis and Luminescence Properties of a New Tripode Containing 2,2'-Bipyrazine Subunits: The tris-[(6-methyl-2,2'-bipyrazine-2-yl)methyl]amine," Tetrahedron Letters (1995), vol. 36, No. 6, pp. 865-868.

CrossFire Beilstein Database Copyright 2007-2009, pp. 1-3. Beilstein Registry No. 708903.

CrossFire Beilstein Database: Copyright 2007-2009, pp. 5-11. Beilstein Registry No. 8957604.

CrossFire Beilstein Database: Copyright 2007-2009, pp. 1-5. Beilstein Registry No. 9068173.

Crossfire Beilstein Database: Copyright 2007-2009, pp. 12-18, Beilstein Registry No. 9075344.

CrossFire Beilstein Database:Copyright 2007-2009, pp. 1-3. Beilstein Registry No. 8958272.

CrossFire Beilstein Database:Copyright 2007-2009, pp. 1-5. Beilstein Registry No. 9511821.

Database Beilstein [Online] Beilstein Institute for Organic Chemisgtry, Frankfurt-Main, DE; 1991, XP002312316 Database accession No. BRN 4622990.

Database Beilstein [Online] Beilstein Institute for Organic Chemistry, Frankfurt-Mail, DE; 1993, XP002312315 Database accessioni No. BRN 5890400; BRB 5896018.

Database Beilstein Beilstein Institute for Organic Chemistry, Frankfurt-Mail, DE; 1997, XP002312314,.

Database CA [Online] Chemical Abstracts Service, Columbus, Ohio, US; Constable, Edwin C. et al: "A double helix dinickel(II) complex with a 1,3-phenylene spacer group through spontaneous self organization" XP002312313 gefunden im STN Database accession No. 1992:186499.

Palilis, L.C., et al., "High efficiency molecular organic light-emitting diodes based on silole derivatives and their exciplexes," Organic Electronics (2003), vol. 4, pp. 113-121.

Piguet, C., et al., "Tridentate binding units as structural patterns for the design of nine-coordinate lanthanide building blocks with predetermined properties," Journal of Alloys and Compounds (2000), vol. 303-304, pp. 94-103.

Slugovc, C., et al., "Generation of Heteroatom-Substituted Carbene Complexes of Indium by Double C-H Activation of Ether and Amine Substrates," Angew, Chem. Int. Ed. (2000), vol. 39, No. 12, pp. 2158-2160.

* cited by examiner

METAL COMPLEXES WITH BIPODAL LIGANDS

RELATED APPLICATIONS

This application is a national stage application (under 35 U.S.C. 371) of PCT/IP2004/011890 filed Oct. 21, 2004 which claims benefit to German application 103 50 722.1 filed Oct. 30, 2003.

Chelate complexes and organometallic compounds will be used in the near future as functional materials in a number of different applications which can be ascribed to the electronics industry in the broadest sense. In the case of organic electroluminescent devices based on organic components (general description of the construction cf. U.S. Pat. No. 4,539,507 and U.S. Pat. No. 5,151,629), and individual components thereof, organic light-emitting diodes (OLEDs), the market introduction has already taken place, as confirmed by the automobile radios and digital cameras with an "organic display" from the Pioneer and Kodak companies. Further products of this type are just about to be introduced. In spite of everything, significant improvements are still necessary here in order to make these displays a true competitor to the liquid-crystal displays (LCDs) which currently dominate the market.

A development in this respect is the improvement of electron-transport materials and blue singlet emitters based on metal chelate complexes, with aluminium and lanthanum chelate complexes being of particular interest here.

A further development that has emerged in recent years is the use of organometallic complexes which exhibit phosphorescence instead of fluorescence (M. A. Baldo, S. Lamansky, P. E. Burrows, M. E. Thompson, S. R. Forrest, Appl. Phys. Lett., 1999, 75, 4-6). For theoretical spin-statistical reasons, an up to four-fold energy and power efficiency is possible using organometallic compounds as phosphorescence emitters. Whether this development will succeed depends on whether it is possible to find corresponding device compositions which are also able to implement these advantages (triplet emission=phosphorescence compared with singlet emission=fluorescence) in the OLEDs. Essential conditions for practical application which may be mentioned here are, in particular, a long lifetime, high stability to heating and a low use and operating voltage in order to enable mobile applications.

In both cases, efficient chemical access to the corresponding chelate complexes or organometallic compounds must be possible. However, this is of particular interest against the background of scarcity of the noble metals ruthenium, osmium, rhodium, iridium, palladium, platinum and gold.

To date, two basic types of construction of OLEDs, which comprise fluorescence or phosphorescence emitters as colouring components, which differ in their layer structure, have been described in the literature. These OLED types are described in detail, for example, in WO 04/058911.

The characteristic data of the OLEDs in accordance with the prior art exhibit, inter alia, the following weak points:
1. The lifetime is in most cases still much too short, which stands in the way of market introduction of OLEDs with a long life.
2. It is evident from the efficiency/brightness curves that the efficiency frequently drops considerably with increasing brightness. This means that the great brightnesses that are necessary in practice can only be achieved by high power consumption. However, large power consumptions require high battery powers of portable equipment (mobile phones, laptops, etc.). In addition, the large power consumption, which is for the most part converted into heat, may result in thermal damage to the display.

In the OLED device explained above, the above-mentioned functional materials have been or are being intensively optimised.

For some time, metal complexes have been employed as ETM (electron-transport material) (for example $AlQ_3$, C. W. Tang et al., Applied Phys. Lett., 1987, 51(12), 913; $ZnQ_2$, S.-J. Jung et al., J. Korean Electrochemical Society, 2000, 3(1), 1), as HBM (hole-blocking material) (for example B—$AlQ_3$, R. Kwong et al., Applied Physics Letters, 2002, 81(1), 162), as matrix material in the EML (emission layer) (for example B—$AlQ_3$, C. H. Chen et al., Proceedings of SPIE—The International Society for Optical Engineering, 1998, 3421, 78), as singlet emitter (for example $AlQ_3$, $ZnQ_2$ and other complexes, S. Tokito et al., Synthetic Metals, 2000, 111-112, 393) and as triplet emitter (for example $Ir(PPy)_3$, WO 00/70655; for example $Ir(TPy)_3$ and $Ir(BTPy)_3$, S. Okada et al., Proceedings of the SID, 2002, 52.2, 1360). Triplet emitters based on platinum complexes have likewise been known for some time, with complexes of tetradentate macrocyclic ligands (for example PtOEP, L. R. Milgrom, Polyhedron, 1988, 7(1), 57; M. A. Baldo, Nature, 1998, 395(6698), 151-154) also being known besides complexes of bidentate ligands (for example Brooks et al., Inorg. Chem., 2002, 41, 3055-3066). These complexes of divalent platinum ($d^8$ configuration) have, like the majority of platinum(II) complexes, a planar or virtually planar structure. In solids, these planar complex units aggregate in such a way that strong and frequently cooperative ligand-ligand, metal-metal or ligand-metal interactions occur.

Besides the individual weak points that are specific to each molecule, the class of the known metal complexes has general weak points, which are described briefly below:
1. Many of the known metal complexes, in particular those which contain main-group metals, such as aluminium, or transition metals having the $d^{10}$ configuration, such as zinc, have a sometimes considerable hydrolysis sensitivity, which can be so pronounced that the metal complex is significantly decomposed even after brief exposure to air. Others, by contrast, such as, for example, the $AlQ_3$ and $ZnQ_2$ used as electron-transport material, tend to adduct water.

The high hygroscopicity of these and similar aluminium and zinc complexes is a crucial practical disadvantage. $AlQ_3$, which is synthesised and stored under normal conditions, always also contains one molecule of water per complex molecule in addition to the hydroxyquinoline ligands (cf., for example: H. Schmidbaur et al., Z. Naturforsch., 1991, 46b, 901-911). This water is extremely difficult to remove. For use in OLEDs, $AlQ_3$ and $ZnQ_2$ therefore have to be subjected to complex purification in complicated, multistep sublimation processes and subsequently stored and handled under a protective-gas atmosphere with exclusion of water. Furthermore, large variations in the quality of individual $AlQ_3$ batches and poor storage stability have been observed (S. Karg, E-MRS Conference, 2000, Strasburg).
2. Many of the known metal complexes have low thermal stability. During vacuum deposition, this inevitably always results in the liberation of organic pyrolysis products, which in some cases, even in small amounts, considerably shorten the lifetime of the OLEDs (for example: R. G. Charles, J. Inorg. Nucl. Chem., 1963, 25, 45; via the thermal stability of $MQ_2$).

3. The strong interaction of the complex units in solids, in particular in the case of planar complexes of $d^8$ metals, such as platinum(II), likewise causes aggregation of the complex units in the emitter layer if the degree of doping exceeds about 0.1%, which is the case in accordance with the current state of the art. This aggregation results in the formation of so-called excimers or exciplexes on excitation (optical or electric). These aggregates frequently have an unstructured, broad emission band, which makes the production of pure basic colours (RGB) considerably more difficult or completely impossible. In general, the efficiency for this transition also drops.

4. In addition, it is evident from the above that the emission colour is highly dependent on the degree of doping, a parameter which can only be controlled precisely with considerable technical effort, in particular in large production plants.

There was therefore a demand for alternative compounds which do not have the above-mentioned weak points.

Surprisingly, it has been found that metal complexes of tetradentate chelating, non-macrocyclic ligands have excellent properties on use as electron-transport material, as hole-blocking material, as matrix material in the EL, as singlet emitter or as triplet emitter, with the respective, specific function being determined by a suitable choice of the metal and the suitable associated ligand. This class of metal complexes and the use thereof as functional materials in opto-electronic components is novel and has not been described in the literature to date, but their efficient preparation and availability as pure substance is of great importance for this.

The present invention thus relates to compounds of structure 1

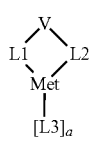

Structure 1 characterised in that they contain a metal Met, coordinated to a tetradentate chelating ligand Lig of structure 2

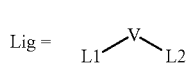

Structure 2 where V is a bridging unit, characterised in that it contains 1 to 40 atoms from the third, fourth, fifth and/or sixth main group and connects the two ligand moieties L1 and L2, which may be identical or different on each occurrence, covalently to one another, and where the two ligand moieties L1 and L2 satisfy structure 3

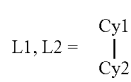

Structure 3 where Cy1 and Cy2, identically or differently on each occurrence, each correspond to a substituted or unsubstituted, saturated, unsaturated or aromatic homo- or heterocyclic ring, preferably an aromatic ring, which is in each case bonded ionically, covalently or coordinatively to the metal (Met) via a ring atom or via an atom bonded exocyclically to the homo- or heterocyclic ring;

and where L3, identically or differently on each occurrence, is a mono- or bidentate, neutral or monoanionic ligand, and where a is 0, 1 or 2.

The bridge V is characterised in that it promotes the formation of mononuclear metal complexes of structure 1, and the formation of coordination polymers does not occur or only occurs to a minor extent on reaction of the ligand of structure 2 with metal compounds.

The homo- or heterocyclic rings Cy1 and Cy2 may also additionally be linked to one another via substituents and thus define a polycyclic, aliphatic or aromatic ring system. They may likewise be linked to one another via a common edge instead of via a single bond.

Preference is given to compounds of structure 1 according to the invention which are characterised in that they are electrically neutral.

Preference is given to compounds of structure 1 according to the invention which are characterised in that L1=L2.

Preference is furthermore given to compounds of structure 1 according to the invention which are characterised in that Cy1 is not identical to Cy2. One of the two rings here preferably bonds via a metal-carbon bond and the other via a donor atom other than carbon, particularly preferably via N, P or S.

Preference is given to compounds of structure 1 according to the invention which are characterised in that the bridging unit V contains 1 to 40 atoms from the third, fourth, fifth and/or sixth main group (group 13, 14, 15 or 16 according to IUPAC) or is a 3- to 6-membered homo- or heterocyclic ring. These form the skeleton of the bridging unit. Particular preference is given to compounds of structure 1 which are characterised in that the linking unit V contains 1 to 6 bridging atoms or is a 3- to 6-membered homo- or heterocyclic ring. The bridging unit V here may also have an asymmetrical structure, i.e. the linking of V to L1 and L2 need not be identical.

Particular preference is given to linking units V in which:
V is $BR^1$, $—(CR_2)R^1B(CR_2)—$, $—O—R^1B—O—$, $—O—(R^1O)B—O—$, $—CR_2O—R^1B—OCR_2—$, $—(CR_2CR_2)R^1B(CR_2CR_2)—$, $C=O$, $C=NR^1$, $C=S$, $CR_2$, $CR(OH)$, $CR(OR^1)$, $C(NR^1)_2$, $—(CR_2)R_2C(CR_2)—$, $—(CR_2CR_2)R_2C(CR_2CR_2)—$, $—(SiR_2)R_2C(SiR_2)—$, $—(SiR_2CR_2)R_2C(CR_2SiR_2)—$, $—(CR_2SiR_2)R_2C(SiR_2CR_2)—$, $—(SiR_2SiR_2)R_2C(SiR_2SiR_2)—$, cis-$RC=CR$, 1,2-$C_6H_4$, 1,3-$C_6H_4$, $SiR_2$, $Si(OH)_2$, $Si(OR^1)_2$, $—(CR_2)R_2Si(CR_2)—$, $—(CR_2CR_2)R_2Si(CR_2CR_2)—$, $—(SiR_2)R_2Si(SiR_2)—$, $—(SiR_2CR_2)R_2Si(CR_2SiR_2)—$, $—(CR_2SiR_2)R_2Si(SiR_2CR_2)—$, $—(SiR_2SiR_2)R_2Si(SiR_2SiR_2)—$, $R^1N$, $—(CR_2)R^1N(CR_2)—$, $—(CR_2CR_2)R^1N(CR_2CR_2)—$, FP, FPO, $R^1P$, $R^1As$, $R^1Sb$, $R^1Bi$, $R^1PO$, $R^1AsO$, $R^1SbO$, $R^1BiO$, $R^1PSe$, $R^1AsSe$, $R^1SbSe$, $R^1BiSe$, $R^1PTe$, $R^1AsTe$, $R^1SbTe$, $R^1BiTe$, $—O—R^1PO—O—$, $—O—(R^1O)PO—O—$, $—CR_2O—R^1PO—OCR_2—$, $—OCR_2—R^1PO—CR_2O—$, O, S, Se, $—(CR_2)O(CR_2)—$, $—(CR_2)S(CR_2)—$, $—(CR_2)(O)S(CR_2)—$ or $—(CR_2)(O)_2S(CR_2)—$ or corresponding asymmetrical analogues;

R is, identically or differently on each occurrence, H, F, Cl, Br, I, $NO_2$, CN, a straight-chain, branched or cyclic alkyl or alkoxy group having 1 to 20 C atoms, where one or more non-adjacent $CH_2$ groups may be replaced by $—R^1C=CR^1—$, $—C≡C—$, $Si(R^1)_2$, $Ge(R^1)_2$, $Sn(R^1)_2$, $C=O$, $C=S$, $C=Se$, $C=NR^1$, $—O—$, $—S—$, $—NR^1—$ or $—CONR^1—$ and where one or more H atoms may be replaced by F, or an aryl, aryloxy or heteroaryl group having 1 to 14 C atoms, which may be substituted by one or more non-aromatic radicals R, where a plurality of substituents R may in turn define a further mono- or polycyclic, aliphatic or aromatic ring system; and $R^1$, $R^2$ are, identically or differently on each occurrence, H or an aliphatic or aromatic hydrocarbon radical having 1 to 20 C atoms.

Particular preference is given to metal complexes as per compounds (1) to (8) according to scheme 1, each of which may also carry one or two additional ligands L3, as described above.

Scheme 1:

Compounds (1)

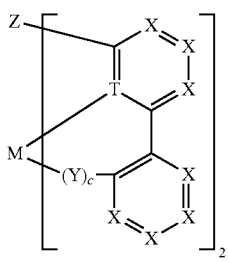

Compounds (2)

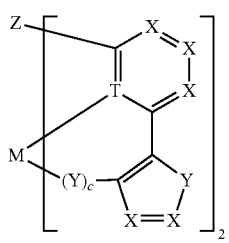

Compounds (3)

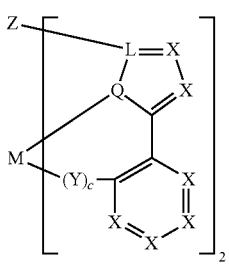

Compounds (4)

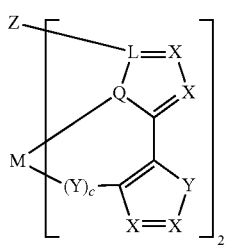

Compounds (5)

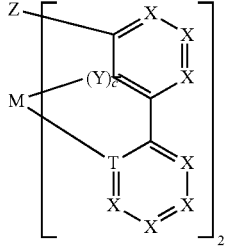

Compounds (6)

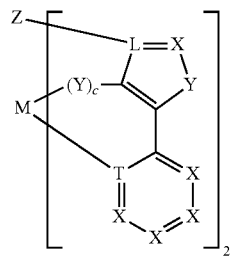

Compounds (7)

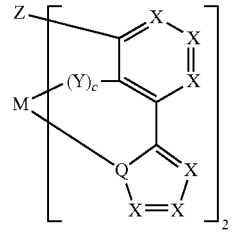

Compounds (8)

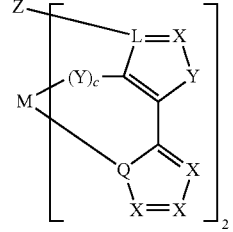

where R, $R^1$ and $R^2$ have the same meaning as described above, and the other symbols and indices have the following meaning:

M is Be, Mg, Ca, Sr, Ba, Al, Ga, In, Tl, Sc, Y, La, Cr, Mo, W, Fe, Ru, Os, Co, Rh, Ir, Ni, Pd, Pt, Cu, Ag, Au, Zn, Cd or Hg;

L is, identically or differently on each occurrence, C, N or P;

Q is, identically or differently on each occurrence, N, O, S, Se or Te;

T is, identically or differently on each occurrence, N or P;

X is, identically or differently on each occurrence, CR, N or P;

Y is, identically or differently on each occurrence, $NR^1$, O, S, Se, Te, SO, SeO, TeO, $SO_2$, $SeO_2$ or $TeO_2$;

Z has the same meaning as described above for V;

c is, identically or differently on each occurrence, 0 or 1.

In addition, preference is likewise given to compounds (9) to (12) according to scheme 2, each of which may also carry one or two additional ligands L3, as described above.

Scheme 2:

Compounds (9)

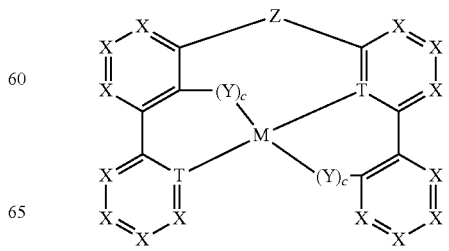

Compounds (10)

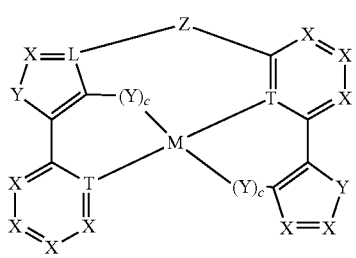

Compounds (11)

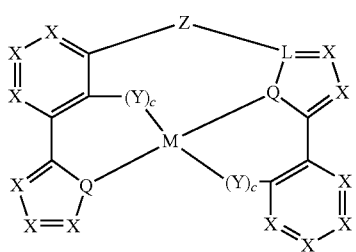

Compounds (12)

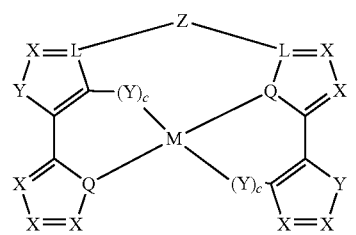

where the symbols and indices M, L, Q, T, X, Y, Z, R, R$^1$, R$^2$ and c have the meaning indicated above.

The invention furthermore relates to compounds which simultaneously have ligands of the type as for compounds (1), (2), (3) and/or (4), i.e. mixed ligand systems. These are described by the formulae (13) to (30)—according to Scheme 3—each of which may also carry one or two additional ligands L3, as described above:

Scheme 3:

Compounds (13)

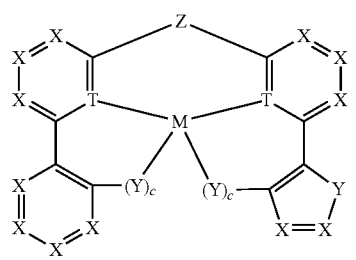

Compounds (14)

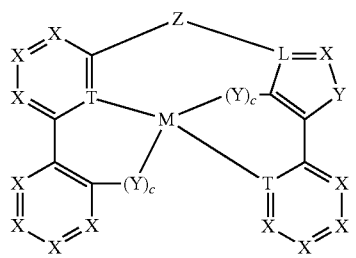

Compounds (15)

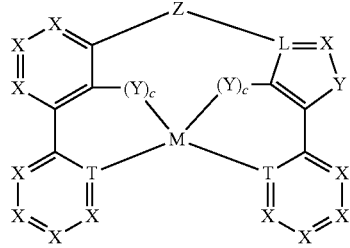

Compounds (16)

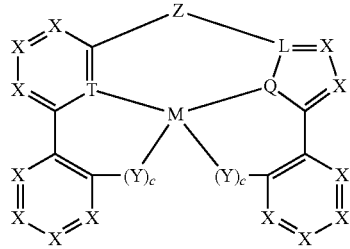

Compounds (17)

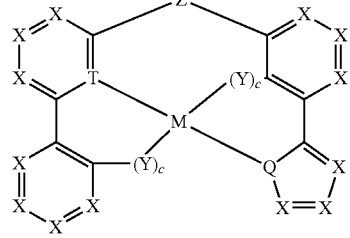

Compounds (18)

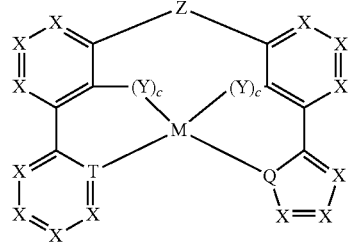

Compounds (19)

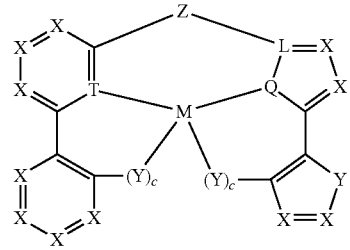

Compounds (20)

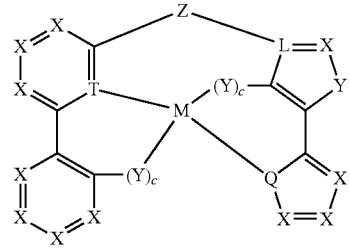

Compounds (21)
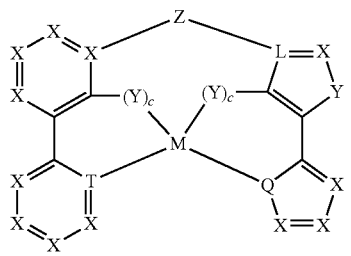

Compounds (22)
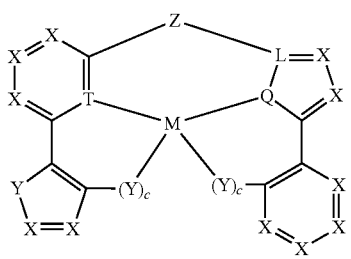

Compounds (23)
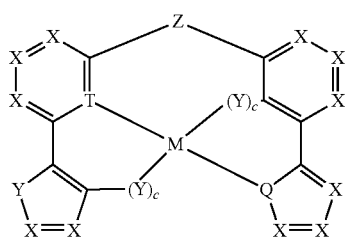

Compounds (24)
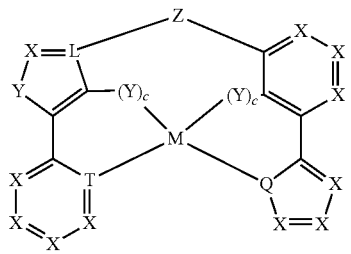

Compounds (25)
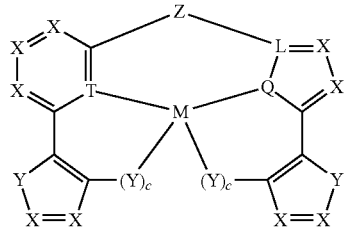

Compounds (26)
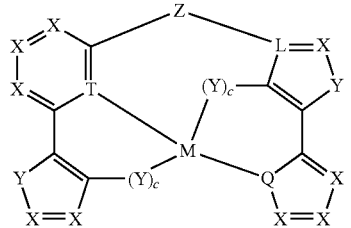

Compounds (27)
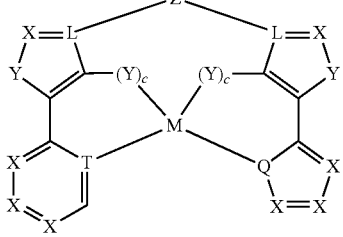

Compounds (28)
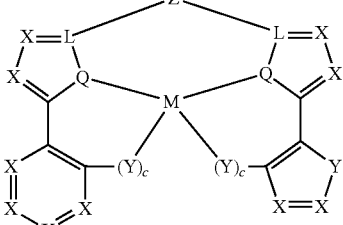

Compounds (29)
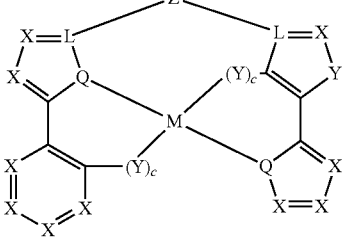

Compounds (30)
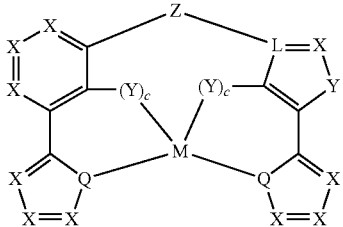

where the symbols and indices M, L, Q, T, X, Y, Z, R, $R^1$, $R^2$ and c have the meaning indicated above.

The compounds of structure 1 or compounds (1) to (30) may optionally carry further mono- or multidentate, cationic, neutral or anionic ligands, as already described above. These are described by ligand L3.

Preference is given to compounds of structure 1 or compounds (1) to (30) which are characterised in that ligand L3, if present, is a bidentate chelating ligand.

In a preferred embodiment of the invention, L3 is a monoanionic ligand which is identical to or different from ligand moieties L1 and L2.

In a further preferred embodiment of the invention, L3 is a ligand of structure (4)

Structure (4)
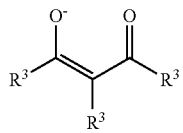

where $R^3$, identically or differently on each occurrence, represents H, a $C_1$ to $C_{20}$ alkyl group, a $C_1$ to $C_{20}$ alkoxy group, a $C_4$ to $C_{20}$ aryl or heteroaryl group or a $C_4$ to $C_{20}$ aryloxy or heteroaryloxy group, and one or more H atoms may be replaced by F.

Preference is given to compounds (1) to (30) according to the invention in which the symbol M=Be, Mg, Pt or Zn, and the index a=0.

Particular preference is given to compounds (1) to (30) according to the invention in which c=0 and M=Pt.

Preference is furthermore given to compounds (1) to (30) according to the invention in which the symbol M=Rh or Ir, particularly preferably M=Ir, and the index a=1 in the case of a bidentate, monoanionic ligand L3 or a=2 in the case of a monodentate monoanionic ligand L3.

Preference is likewise given to compounds (1) to (30) according to the invention in which the symbol L=C or N, particularly preferably L=C.

Preference is likewise given to compounds (1) to (30) according to the invention in which the symbol Q=O or S.

Preference is likewise given to compounds (1) to (30) according to the invention in which the symbol T=N.

Preference is likewise given to compounds (1) to (30) according to the invention in which the symbol X=CR or N.

Preference is likewise given to compounds (1) to (30) according to the invention in which the symbol Z=BR$^1$, CR$_2$, CO, SiR$^1{}_2$, R$^1$N, FP, FPO, R$^1$P, R$^1$PO, —CR$_2$CR$_2$—, —CR$_2$—O—CR$_2$—, —O—(OR$^1$)PO—O—, cis-CR=CR, —CR$_2$—BR$^1$—CR$_2$—, —CR$_2$—CO—CR$_2$—, —CR$_2$—CR$_2$—CR$_2$— or —CR$_2$—NR$^1$—CR$_2$.

Preference is likewise given to compounds (1) to (30) according to the invention in which the symbol R=H, F, Cl, Br, I, CN, a straight-chain, branched or cyclic alkyl or alkoxy group having 1 to 6 C atoms or an aryl or heteroaryl group having 3 to 10 C atoms, which may be substituted by one or more non-aromatic radicals R, where a plurality of substituents R, both on the same ring and also on the two different rings, may together in turn define a further mono- or polycyclic, aliphatic or aromatic ring system.

In compounds (1) to (30), the radicals R may define aliphatic, olefinic or aromatic ring systems.

If the radicals R define aromatic ring systems in compounds (1) to (30), these are preferably benzene, 1- or 2-naphthalene, 1-, 2- or 9-anthracene, 2-, 3- or 4-pyridine, 2-, 4- or 5-pyrimidine, 2-pyrazine, 3- or 4-pyridazine, triazine, 2-, 3-, 4-, 5-, 6-, 7- or 8-quinoline, 2- or 3-pyrrole, 3-, 4-, 5-pyrazole, 2-, 4-, 5-imidazole, 2-, 3-thiophene, 2-, 3-selenophene, 2- or 3-furan, 2-(1,3,4-oxadiazole), indole or carbazole.

The compounds according to the invention are distinguished by the following general properties:

1. The compounds according to the invention—in contrast to many known metal complexes which undergo partial or complete pyrolytic decomposition on sublimation—have high thermal stability. This applies in particular to the platinum and iridium complexes according to the invention with tetradentate chelating ligands which, besides dative coordination via a hetero atom, also contain at least one aryl carbon-platinum or -iridium bond. The high stability of the compounds according to the invention results in a significant increase in the lifetime on use in corresponding devices.
2. The compounds according to the invention have no evident hydrolysis or hygroscopicity. Storage for a number of days or weeks with ingress of air and water vapour does not result in any changes to the substances. The adduction of water onto the compounds could not be detected. This has the advantage that the substances can be purified, transported, stored and prepared for use under simpler conditions.
3. The compounds according to the invention—employed as electron-transport material in electroluminescent devices—result in high efficiencies therein, in particular independently of the current densities used. Very good efficiencies are thus also achieved in the case of high current densities, i.e. high brightnesses.
4. The compounds according to the invention—employed as hole-blocking material in electroluminescent devices—result in high efficiencies therein, in particular independently of the current densities used. Very good efficiencies are thus also achieved in the case of high current densities. In addition, the materials according to the invention are stable to holes, which is not the case to an adequate extent in the case of other metal complexes, for example AlQ$_3$ and analogous compounds (Z. Popovic et al., Proceedings of SPIE, 1999, 3797, 310-315).
5. The compounds according to the invention—employed in electroluminescent devices as emission material in pure form or as emission material doped into a matrix material or as matrix material in combination with a dopant—result in high efficiencies, with the electroluminescent devices being distinguished by steep current/voltage curves and particularly by long operating service lives.
6. The compounds according to the invention are shaped by the structural definitions in such a way that they are non-planar and thus aggregation with formation of strong metal-metal, metal-ligand or ligand-ligand interactions is suppressed.
7. Suppression of the aggregation of these compounds results firstly in narrow emission bands and thus purer emission colours. Secondly, the emission colour is independent of the degree of doping over broad ranges, which is a major advantage for industrial applications.
8. Without wishing to be tied to a particular theory, the rigid structure of the compounds according to the invention is conducive to high quantum efficiencies of the emission transitions.
9. The compounds according to the invention can be prepared in a readily reproducible manner in reliably high purity and have no batch variations.
10. The compounds according to the invention in some cases have excellent solubility in organic solvents, it being possible for the solubility to be customised through a suitable choice of the substitution pattern, for example by introduction of branched alkyl chains into bridge V or Z. These materials can thus also be processed from solution by coating or printing techniques. Even in the case of conventional processing by evaporation, this property is advantageous since cleaning of the plants or shadow masks employed by washing is thus considerably simplified.

The present invention likewise relates to compounds (31) to (60) according to scheme 4:

Scheme 4

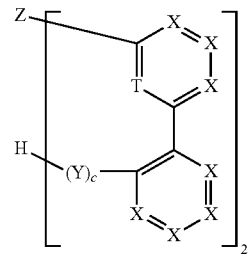

Compounds (31)

Compounds (32)
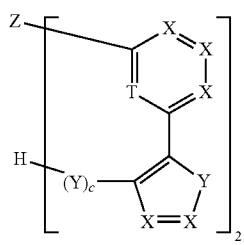
Compounds (33)
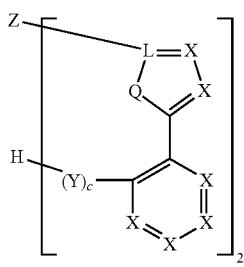
Compounds (34)
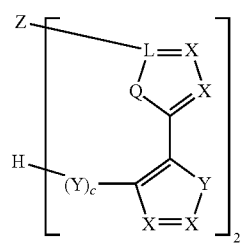
Compounds (35)
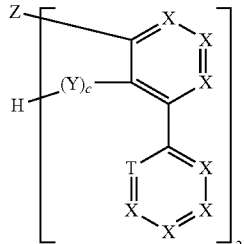
Compounds (36)
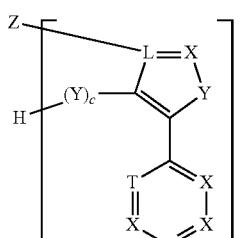
Compounds (37)
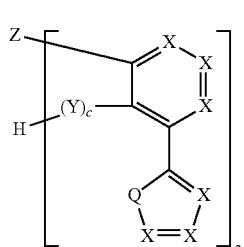
Compounds (38)
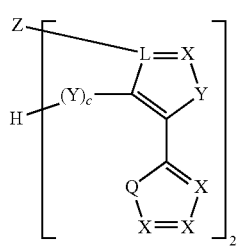
Compounds (39)
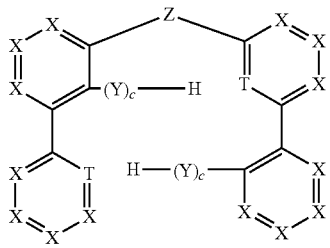
Compounds (40)
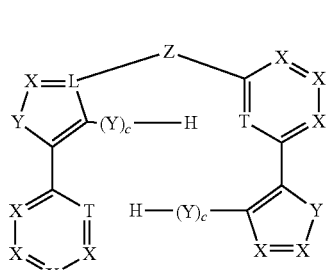
Compounds (41)
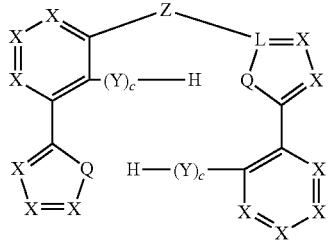
Compounds (42)
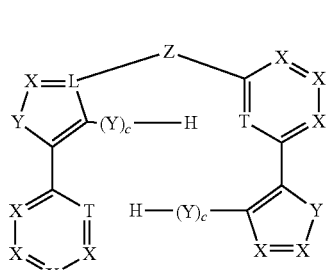
Compounds (43)
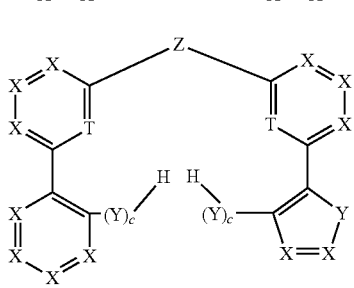

Compounds (44)
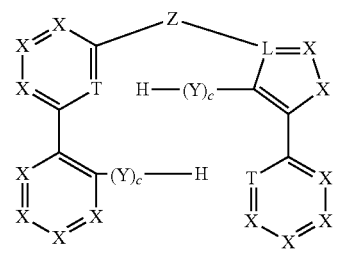
Compounds (45)
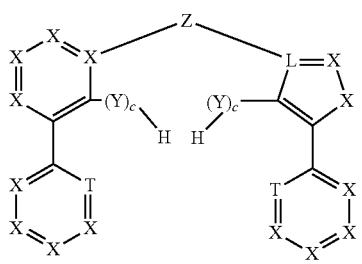
Compounds (46)
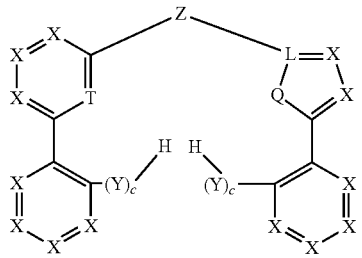
Compounds (47)
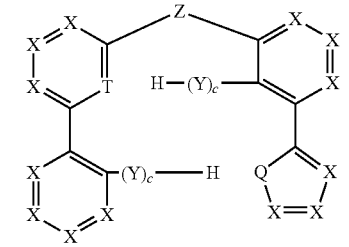
Compounds (48)
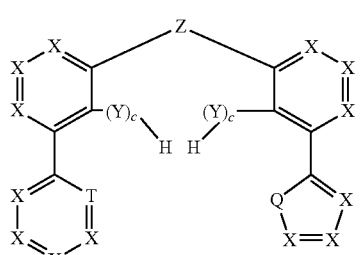
Compounds (49)
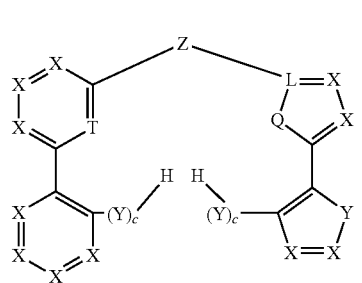
Compounds (50)
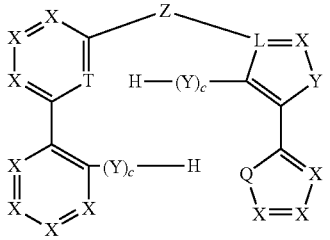
Compounds (51)
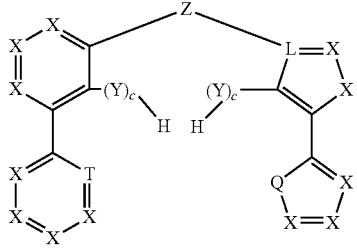
Compounds (52)
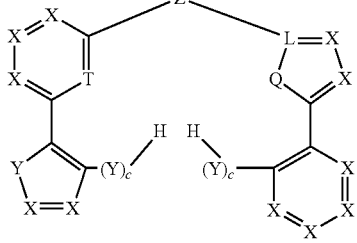
Compounds (53)
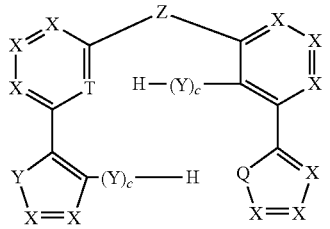
Compounds (54)
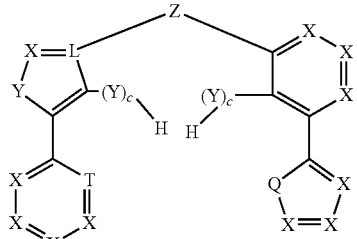
Compounds (55)
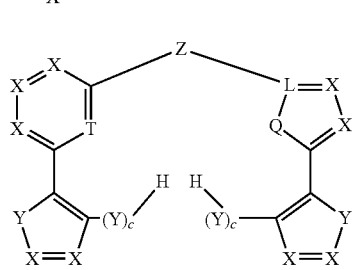

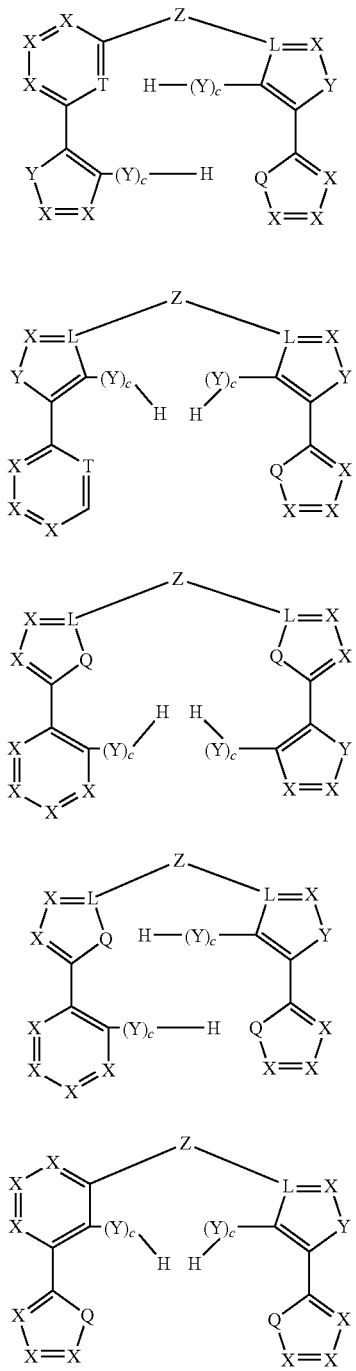

Compounds (56)

Compounds (57)

Compounds (58)

Compounds (59)

Compounds (60)

where the symbols and indices Q, L, T, X, Y, Z, R, $R^1$, $R^2$ and c have the meaning indicated above, apart from the compounds bis(6-phenyl-2-pyridyl)methane [CAS 362602-93-5], bis(6-phenyl-2-pyridyl)ketone [CAS 217177-35-0], bis(6-(1-hydroxy-3,5-di-tert-butyl)phenyl-2-pyridyl)methanol [CAS 367525-74-4], 2,2'-thiobis(3-cyano-2,4-diphenyl)pyridine [CAS 160598-76-5], bis(6-(3-phenyl)phenyl-2-pyridyl)methane [CAS 57476-80-9] and isomers [CAS 57476-79-6].

The above compounds (31) to (60) have already been described in detail in structure 2

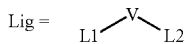

and follow the same concept (V=Z).

These compounds represent the ligands of the compounds of structure 1 according to the invention and are thus valuable intermediates on the route to these compounds.

Compounds (31) to (60) according to the invention can be prepared by common organic reactions, which is confirmed below with reference to a sufficient number of examples. Thus, compounds (31) can be obtained starting from di(6-bromo-2-pyridyl)ketone (WO 98/22148) by reaction with aliphatic or aromatic lithium or Grignard reagents, giving a dipyridylmethanol. This can then be fluorinated, chlorinated or brominated, for example by reaction with halogenating agents, such as diethylaminosulfur trifluoride (DAST), thionyl chloride or phosphorus tribromide respectively. Alkylation of the hydroxyl group with formation of an ether can likewise easily be carried out. Final Suzuki coupling with arylboronic acids then gives the compounds (31). This reaction sequence is shown in scheme 5 with reference to a specific example—methylation, fluorination, coupling with phenylboronic acid—and gives compound (31) where c=0.

Scheme 5:

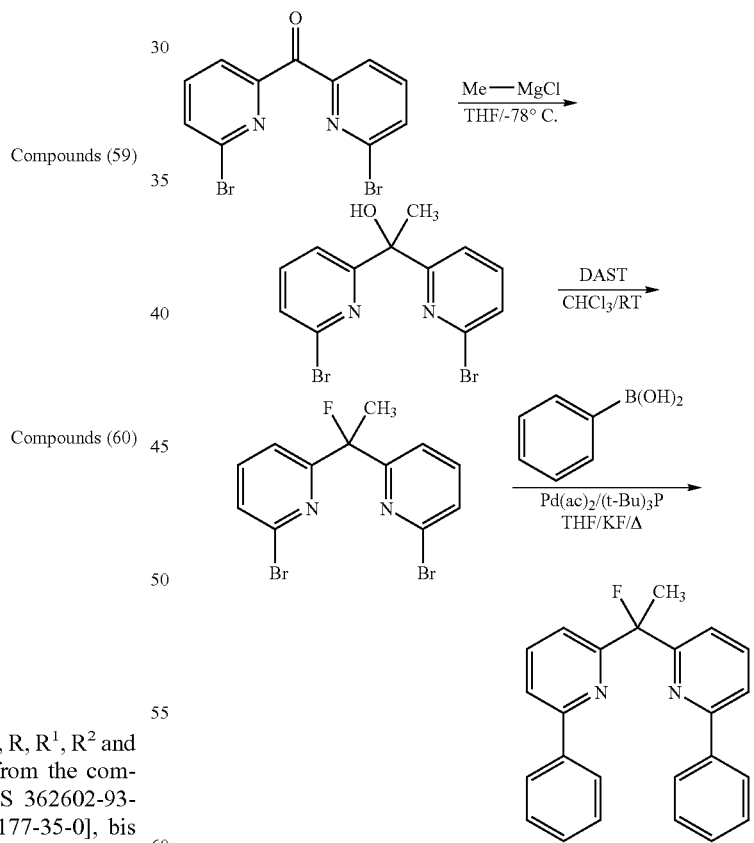

An analogous reaction sequence using tetrahydropyranyl-protected phenolboronic acids, which can be prepared from the corresponding bromophenols by protection using dihydropyran, subsequent Grignard reaction and reaction with a boric acid ester, gives, after protecting group removal, compounds of type (31) where c=1 (scheme 6).

Scheme 6:

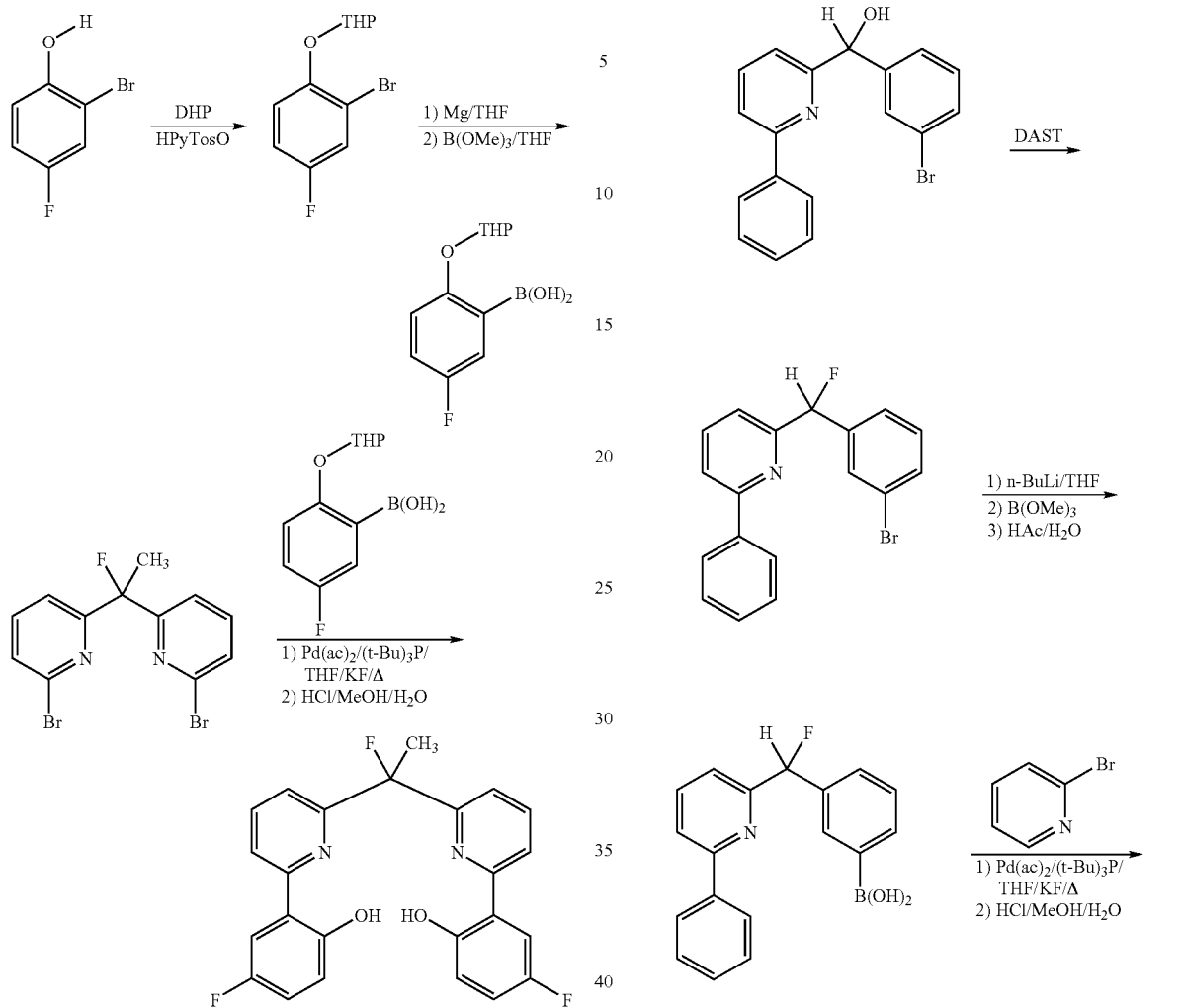

Compounds (32) to (38) can also be prepared in an analogous manner through the use of the corresponding 5- and 6-membered heterocyclic compounds.

Compounds of type (39) and (40) can be prepared, for example, in accordance with the reaction sequence shown in scheme 7 with reference to a specific example. It is of course also possible to obtain a multiplicity of further compounds here by variation of the starting materials (aryl halides or boronic acids).

Scheme 7:

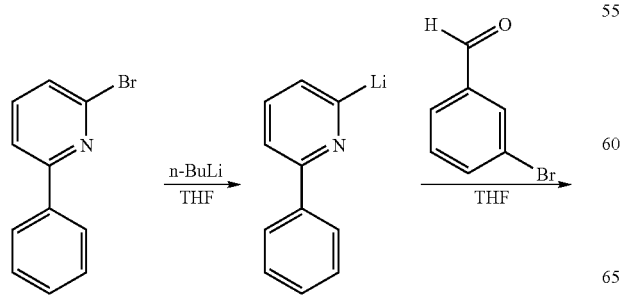

Finally, it should be noted that compounds (41) to (60) are also accessible in an entirely analogous manner through the use of analogous reaction sequences.

Starting from 2-lithio-6-phenylpyridine (Gros et al., J. Org. Chem., 2003, 68(5), 2028-2029) and analogues thereof, it is possible to prepare ligands according to the invention which carry hetero atoms in bridge V or Z, it being possible to use electrophiles containing the hetero atom which are suitable as further synthones. Suitable electrophiles are, inter alia, dichloroarylboranes, dichloroalkyl- or -arylsilanes or dichloroaryl- or -alkylphosphines, as shown in scheme 8.

Scheme 8:

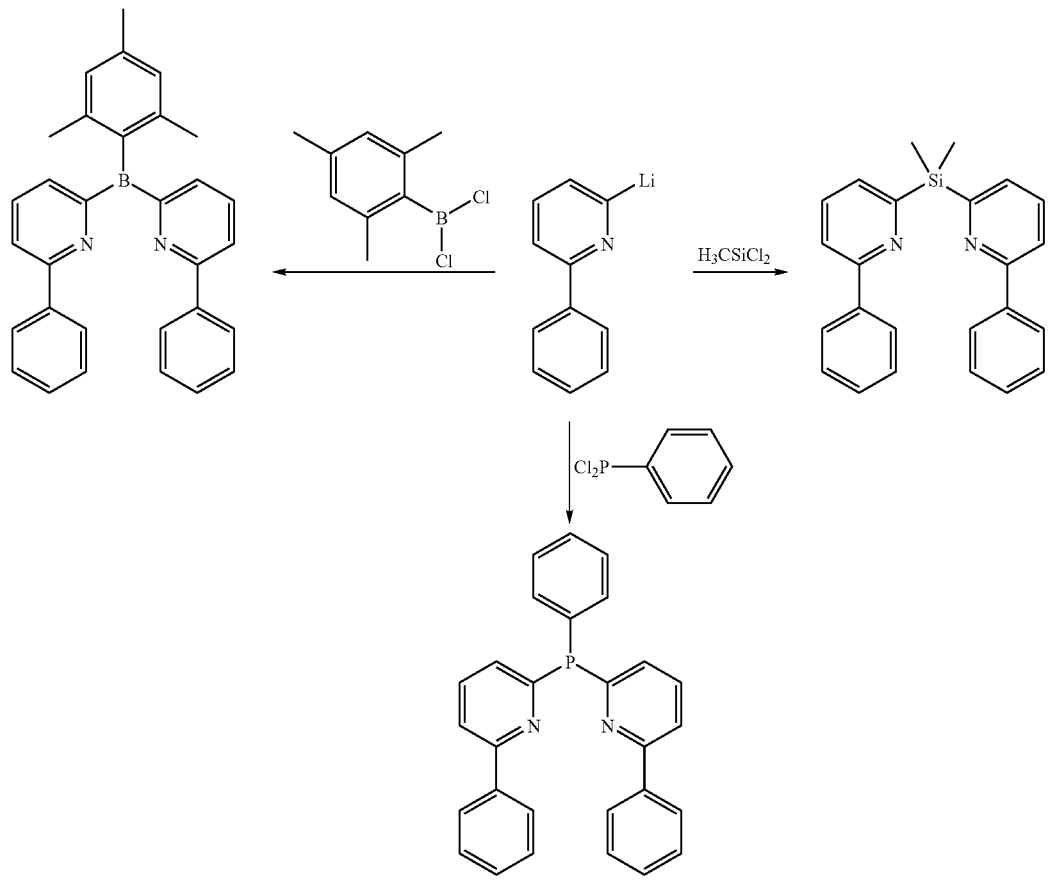

Compounds (1) to (30) according to the invention can in principle be prepared by various processes; however, the novel processes described below have proven particularly suitable.

The present invention therefore furthermore relates to a process for the preparation of compounds (1) to (30) by reaction of the tetradentate chelating ligands as per compounds (31) to (60) with metal alkoxides of compound (61), with metal ketoketonates of compound (62), metal halides, carboxylates, nitrates and sulfates of compound (63) and alkyl- or arylmetal compounds of compound (64), Compounds (61)

$M(OR^1)_n$

Compounds (62)

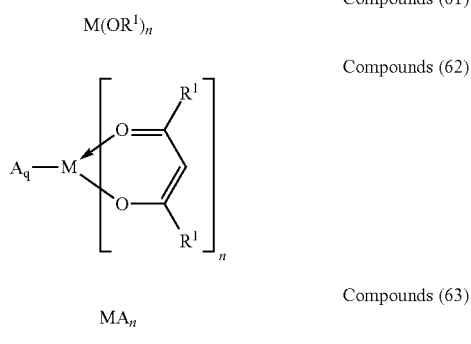

Compounds (63)

$MA_n$

Compounds (64)

$(R^1)_2ML'_2$ where the symbols M and $R^1$ have the meaning indicated under scheme 1, and A=F, Cl, Br, I, OH, formate, acetate, propionate, benzoate, nitrate or sulfate, and L' is a monodentate ligand from the group of the ethers, such as, for example, THF, the amines, such as, for example, trimethylamine or pyridine, the phosphines, such as, for example, triphenylphosphine, or the sulfoxides, such as, for example, DMSO, and n=1, 2 or 3 and q=0, 1, 2 or 3, preferably 0, 1 or 2. Compound (62) here may also be charged. If desired, Lewis acids, such as, for example, aluminium chloride or antimony pentafluoride or -chloride, or Brönsted bases, such as, for example, amines, or alkylating agents, such as, for example, organolithium or Grignard compounds, can be added as auxiliary agents.

It may furthermore be advantageous to carry out the reaction in a number of individual steps for introduction of the individual ligands. Thus, for example, it may be preferred for the ligand Lig to be introduced first and for the complex also to comprise further auxiliary ligands (for example halides), which are then replaced by a bidentate chelating ligand L3 in a further step. It is likewise possible, for example, to introduce the ligand moieties L1 and L2 into the complex first, and then to link them to the bridging unit V or Z in a subsequent step.

Compounds (1) to (30) can thus be obtained in high purity, preferably >99% (determined by $^1$H-NMR and/or HPLC).

Inter alia, the examples of compounds (1) to (66) shown below can be prepared using the synthetic methods explained here.
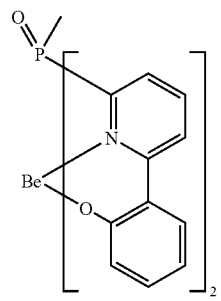
Example 1
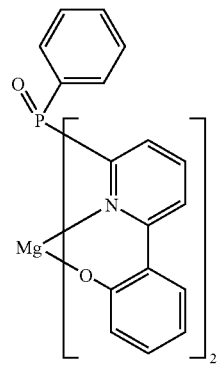
Example 2
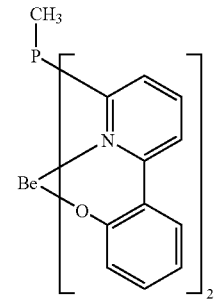
Example 3
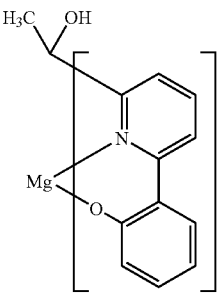
Example 4
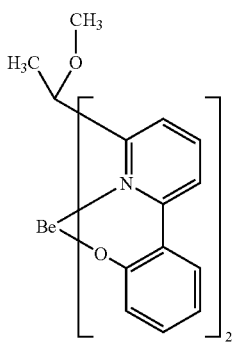
Example 5
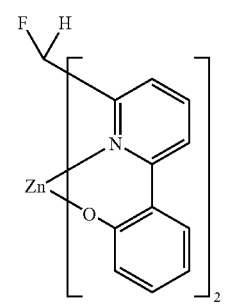
Example 6
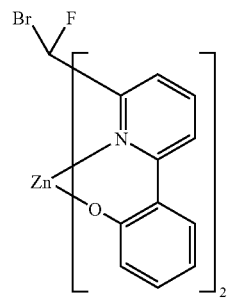
Example 7
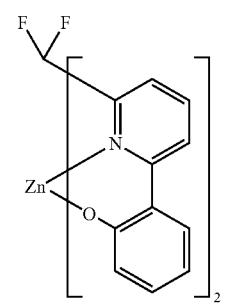
Example 8

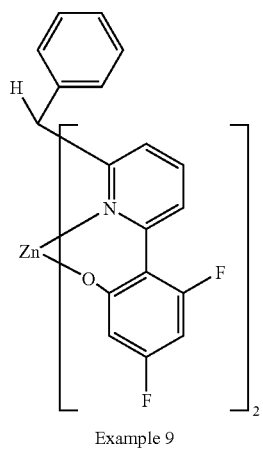
Example 9
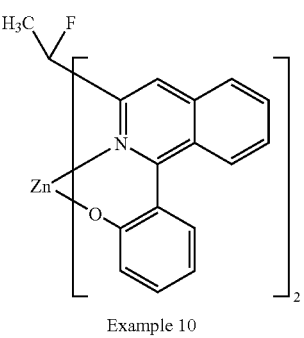
Example 10
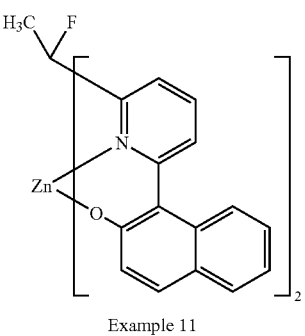
Example 11
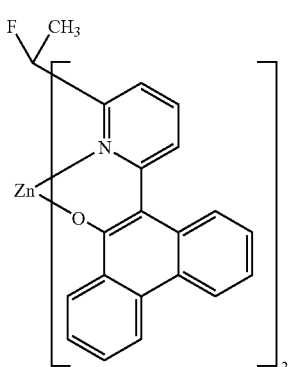
Example 12
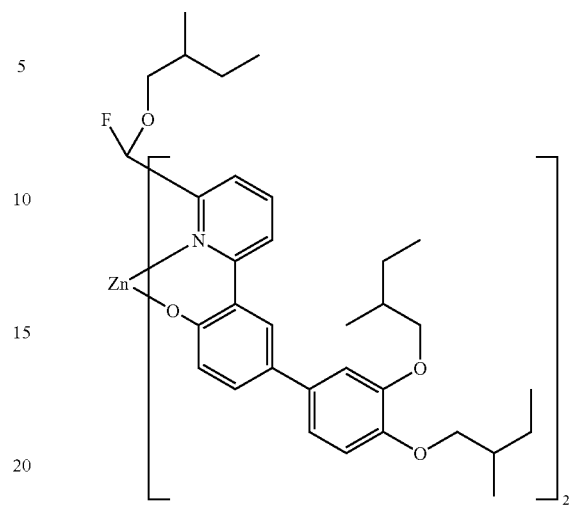
Example 13
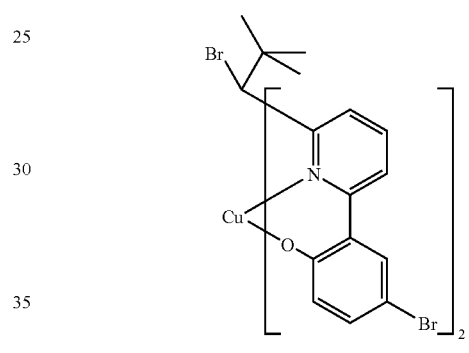
Example 14
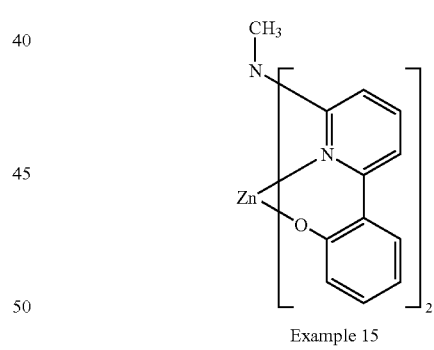
Example 15
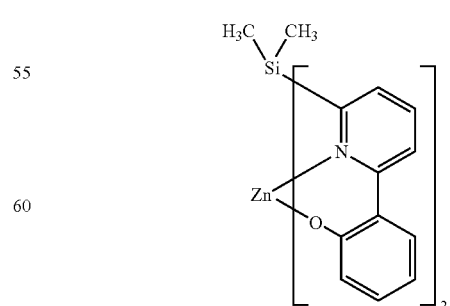
Example 16

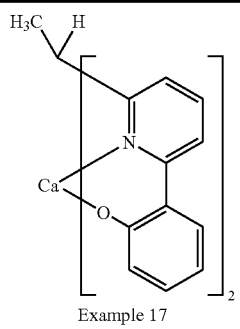
Example 17
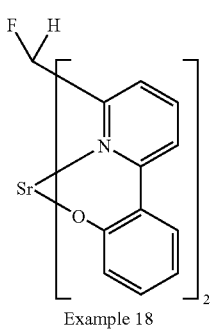
Example 18
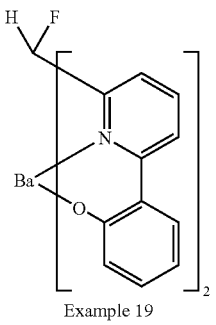
Example 19
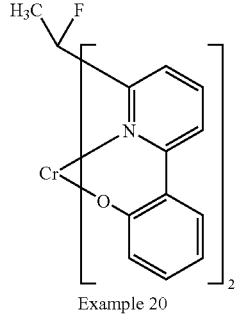
Example 20
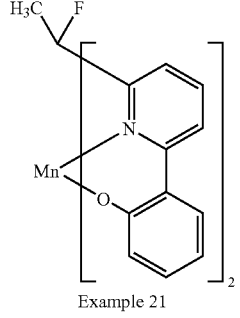
Example 21
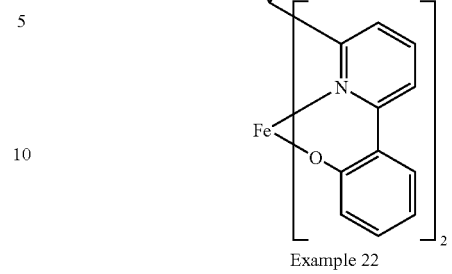
Example 22
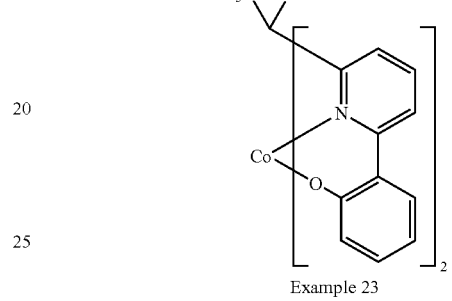
Example 23
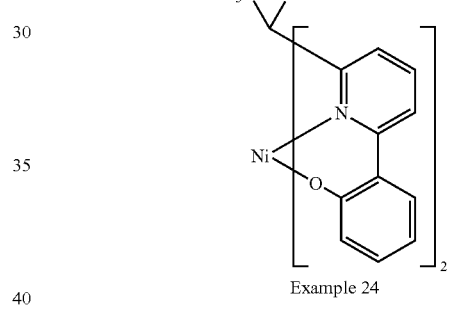
Example 24
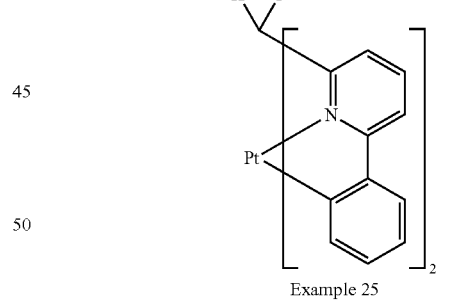
Example 25
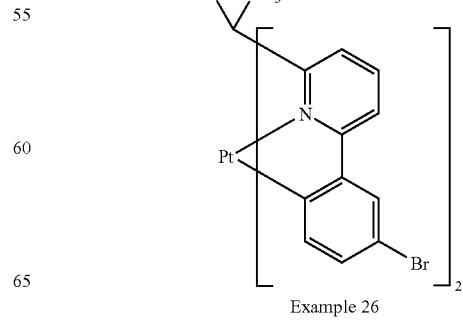
Example 26

-continued
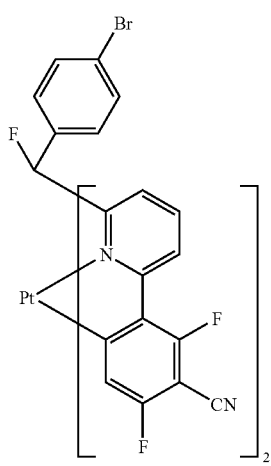
Example 27
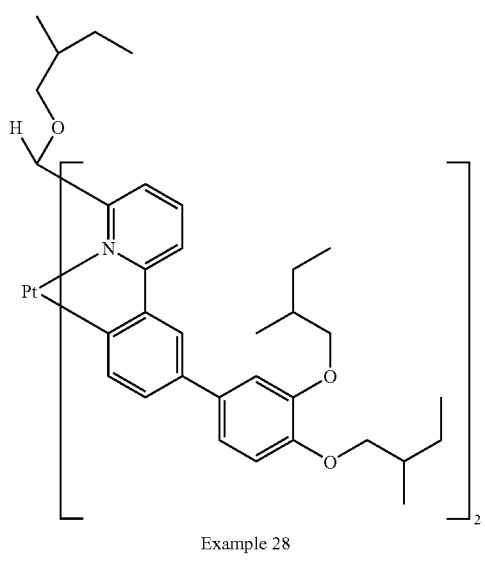
Example 28
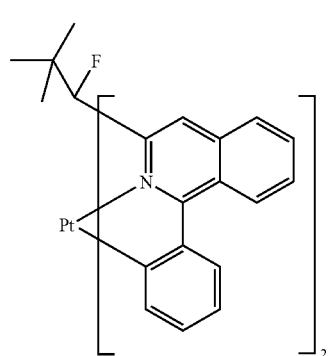
Example 29
-continued
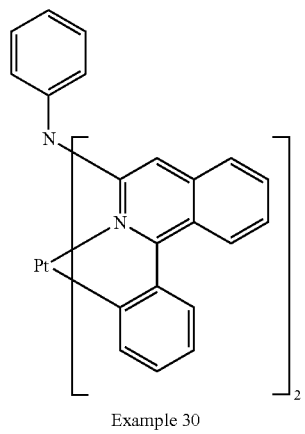
Example 30
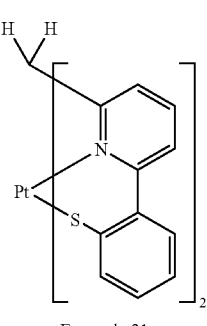
Example 31
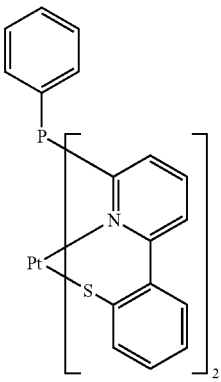
Example 32
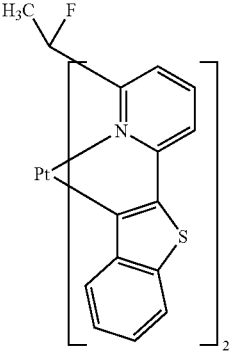
Example 33

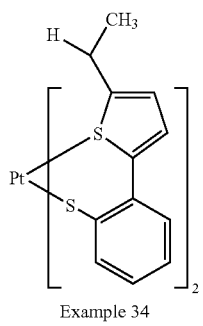
Example 34
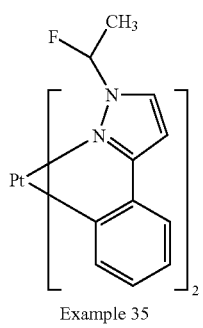
Example 35
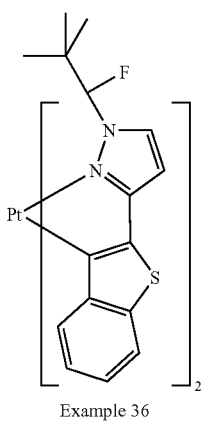
Example 36
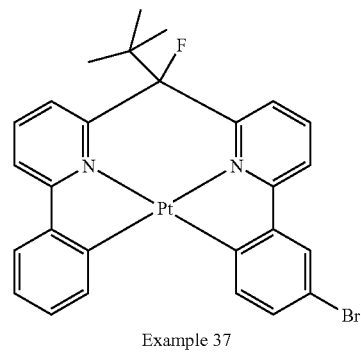
Example 37
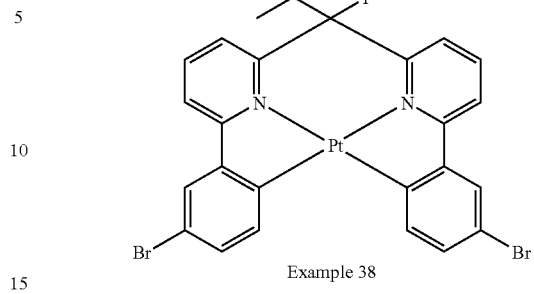
Example 38
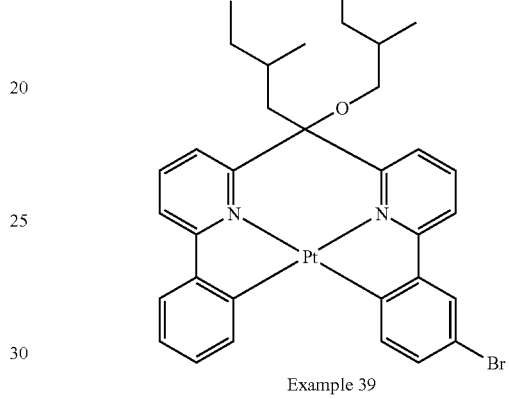
Example 39
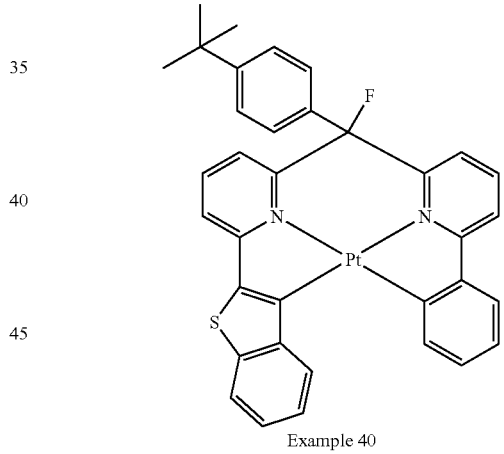
Example 40
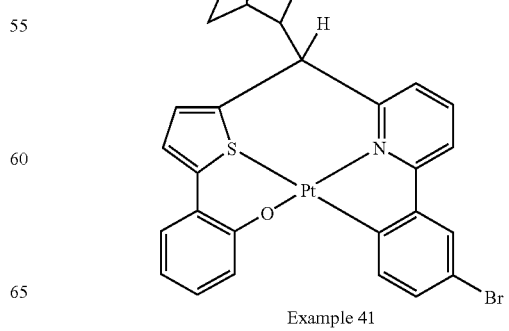
Example 41

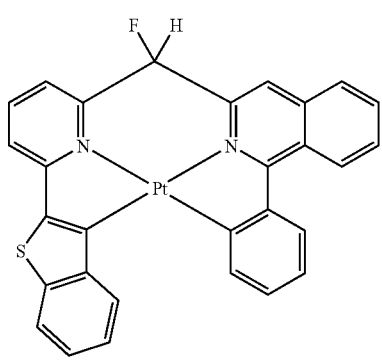
Example 42
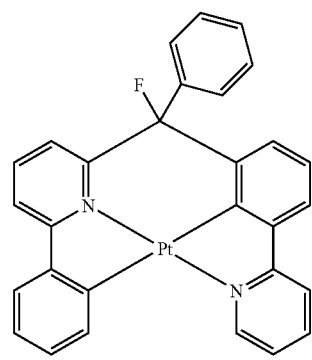
Example 43
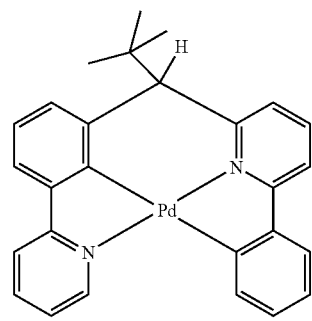
Example 44
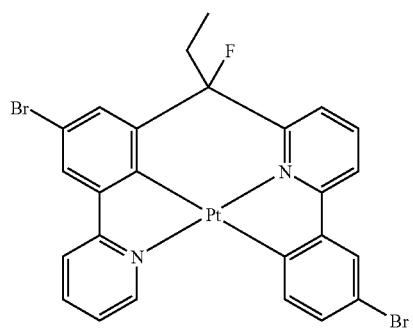
Example 45
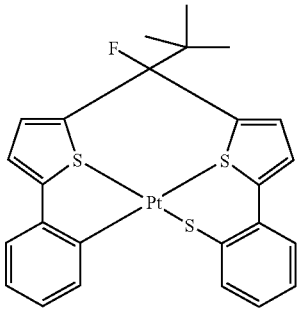
Example 46
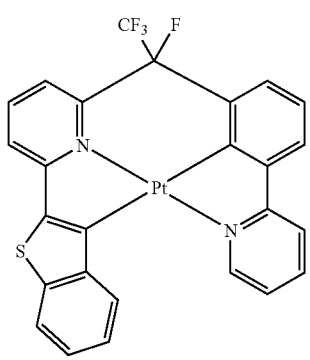
Example 47
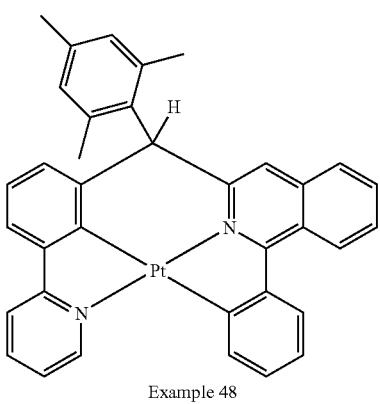
Example 48
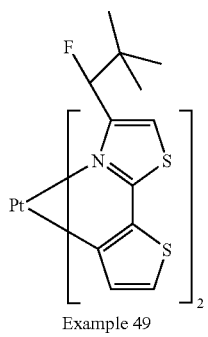
Example 49

-continued
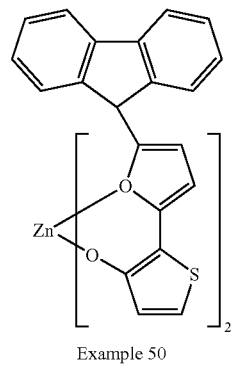
Example 50
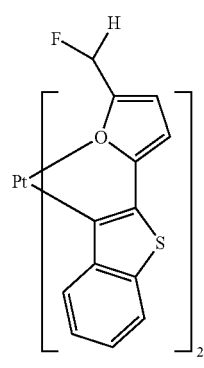
Example 51
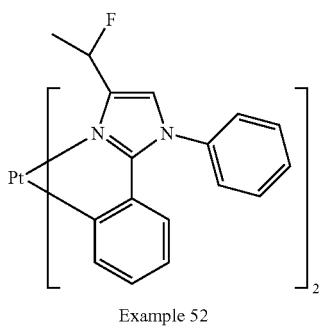
Example 52
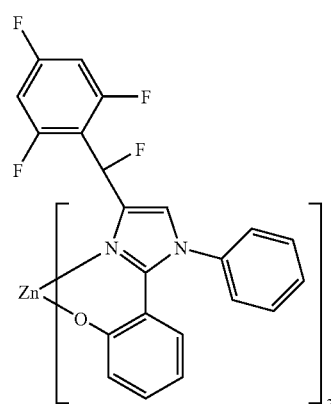
Example 53
-continued
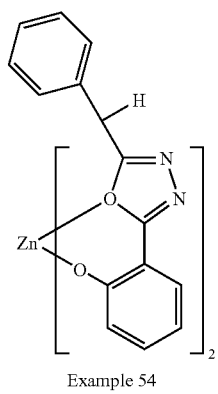
Example 54
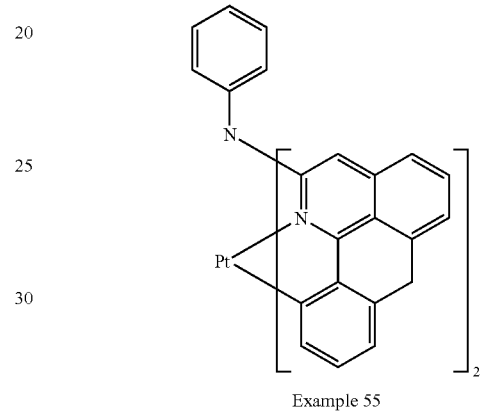
Example 55
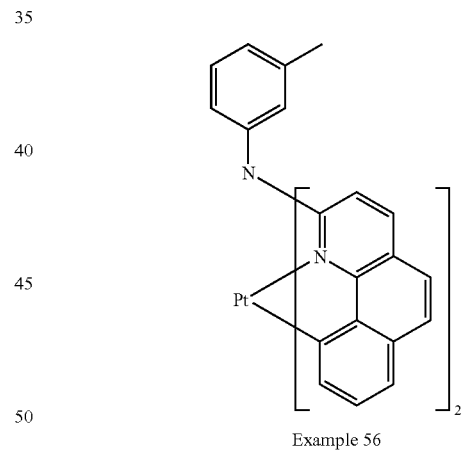
Example 56
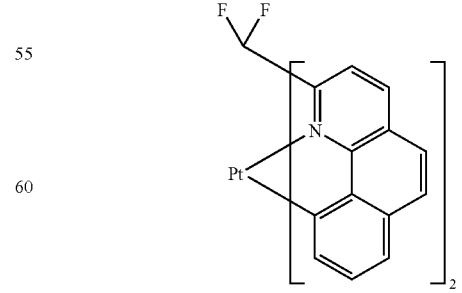
Example 57

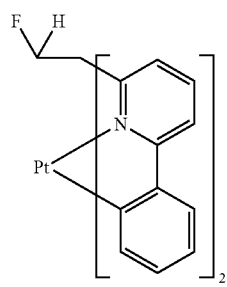
Example 58
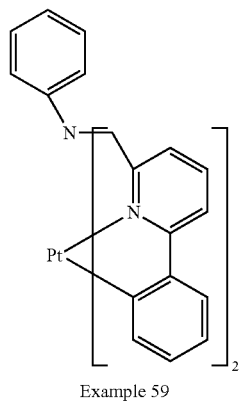
Example 59
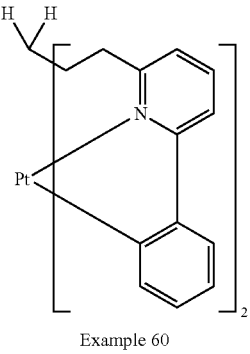
Example 60
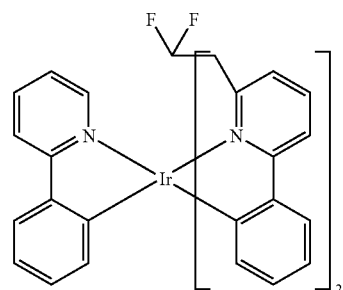
Example 61
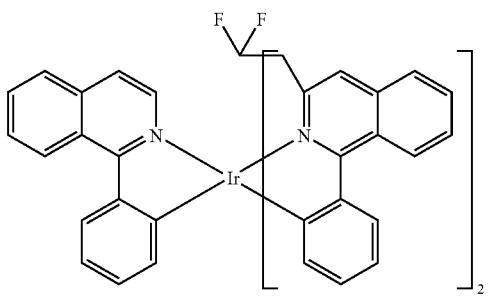
Example 62
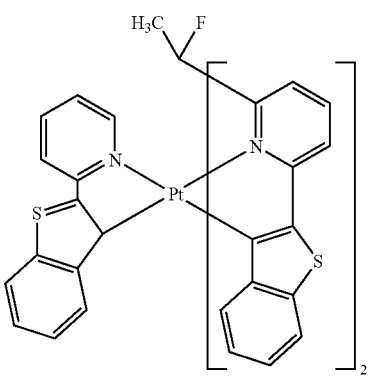
Example 63
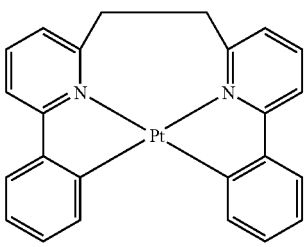
Example 64
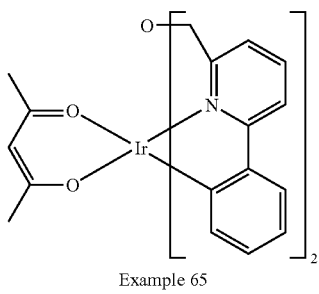
Example 65
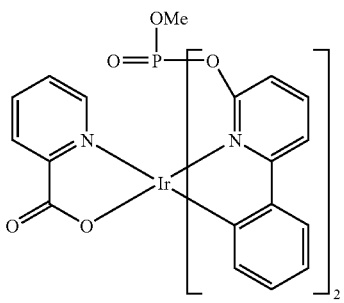
Example 66

In general, structures which contain the above structural elements as substructures, for example the compounds according to scheme 9, are also regarded as according to the invention.

Scheme 9:

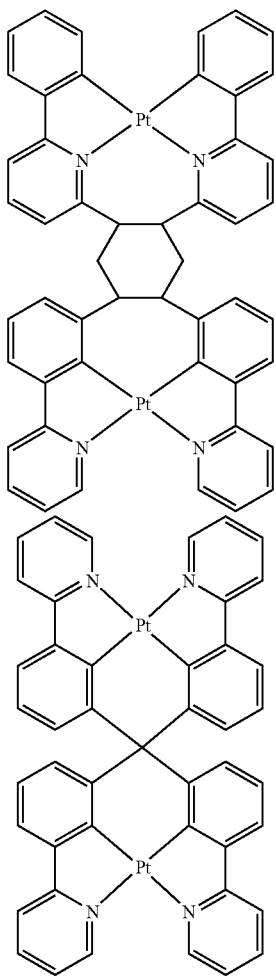

The compounds according to the invention described above—for example compounds according to Examples 7, 14, 26, 27, 37, 38, 39, 41, 45—can also be used as comonomers for the production of corresponding conjugated, partially conjugated or non-conjugated polymers or dendrimers—for example compounds according to Examples 14 and 26. The corresponding polymerisation is preferably carried out here via the halogen functionality. Thus, they can be polymerised, inter alia, into soluble polyfluorenes (for example in accordance with EP 842208 or WO 00/22026), polyspirobifluorenes (for example in accordance with EP 707020 or EP 894107), poly-para-phenylenes (for example in accordance with WO 92/18552), polydihydrophenanthrenes (for example in accordance with DE 10337346.2), polyindenofluorenes (for example in accordance with WO 04/041901 or EP 03014042.0), polycarbazoles (for example in accordance with DE 10304819.7 or DE 10328627.6), polythiophenes (for example in accordance with EP 1028136), polyvinylcarbazoles or also polyketones, or into copolymers comprising two or more of these units.

The invention thus furthermore relates to conjugated, partially conjugated or non-conjugated polymers or dendrimers containing one or more compounds (1) to (30), where at least one of the radicals R defined above represents a bond to the polymer or dendrimer.

The metal complexes according to the invention can furthermore also be functionalised further by the above-mentioned types of reaction, for example, and thus converted into extended metal complexes. An example which may be mentioned here is functionalisation using arylboronic acids by the SUZUKI method or using amines by the HARTWIG-BUCHWALD method.

Compounds (1) to (30) according to the invention described above, the polymers and dendrimers containing compounds of type (1) to (30) as comonomers, and the extended metal complexes are used as active components in electronic components, such as, for example, organic light-emitting diodes (OLEDs), organic integrated circuits (O-ICs), organic field-effect transistors (OFETs), organic thin-film transistors (OTFTs), organic solar cells (O-SCs) or organic laser diodes (O-lasers).

The invention thus also relates to the use of compounds (1) to (30) according to the invention described above, the polymers and dendrimers containing compounds of type (1) to (30) as comonomers, and the extended metal complexes in electronic and/or optical devices, such as, for example, organic light-emitting diodes (OLEDs), organic integrated circuits (O-ICs), organic field-effect transistors (OFETs), organic thin-film transistors (OTFTs), organic solar cells (O-SCs) or organic laser diodes (O-lasers).

The invention furthermore relates to electronic and/or optical devices, in particular organic light-emitting diodes (OLEDs), organic integrated circuits (O-ICs), organic field-effect transistors (OFETs), organic thin-film transistors (OTFTs), organic solar cells (O-SCs) or organic laser diodes (O-lasers), comprising one or more of compounds (1) to (30) according to the invention, the polymers and dendrimers containing compounds of type (1) to (30) as comonomers, and the extended metal complexes.

The present invention is explained in greater detail by the following examples, without wishing to be restricted thereto. The person skilled in the art will be able to prepare further complexes according to the invention or use the process according to the invention from the descriptions without inventive step.

The OLEDs comprising one or more of the compounds according to the invention can be prepared by processes familiar to the person skilled in the art, as described, for example, in WO 04/058911 and DE 10317556.3.

EXAMPLES

The following syntheses were, unless indicated otherwise, carried out under a protective-gas atmosphere in dried solvents. The starting materials were purchased from ALDRICH or ABCR [methylmagnesium chloride 3M in THF, diethylaminosulfur trifluoride (DAST), benzeneboronic acid, potassium fluoride (spray-dried), tri-tert-butylphosphine, palladium(II) acetate, potassium tetrachloroplatinate]. Di(6-bromo-2-pyridyl)ketone was prepared as described in WO 98/22148. cis-Dimethyl-di($\eta^1$-S-dimethylsulfoxidyl)platinum(II) was prepared as described by C. Eaborn et al., J. Chem. Soc., Dalton Trans., 1981, 933-938.

Ligand Synthesis

Example 1

1,1-Bis(6-phenyl-2-pyridyl)-1-fluoroethane a) 1,1-Bis(6-bromo-2-pyridyl)ethan-1-ol

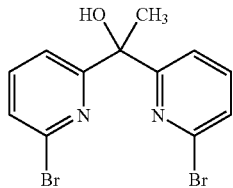 [SMILES: CC(O)(c1cccc(Br)n1)c1cccc(Br)n1]

113 ml (340 mmol) of a 3M methylmagnesium chloride solution in THF were added dropwise with vigorous stirring to a suspension, cooled to −78° C., of 102.6 g (300 mmol) of di(6-bromo-2-pyridyl)ketone in 1000 ml of THF at such a rate that a temperature of −60° C. was not exceeded. When the addition was complete, the mixture was stirred for a further 30 min., then 50 ml of ethanol were added dropwise, the mixture was warmed to 0° C., and 60 ml of semi-saturated ammonium chloride solution were added. The reaction mixture was filtered, the salts were washed twice with 100 ml of THF each time, and the filtrate was evaporated to dryness in a rotary evaporator. The oily residue was taken up in 1000 ml of dichloromethane, and the organic phase was washed three times with 300 ml of water and dried over magnesium sulfate. Stripping off of the dichloromethane left 106.0 g (296 mmol), corresponding to a yield of 98.6%, of the crude product having a purity of about 95% according to $^1$H-NMR as a yellow-brown oil, which was reacted further without purification.

$^1$H-NMR (CDCl$_3$): δ [ppm]=7.77 (d, $^3J_{HH}$=7.8 Hz, 2H), 7.53 (dd, $^3J_{HH}$=7.8 Hz, $^3J_{HH}$=7.8 Hz, 2H), 7.34 (d, $^3J_{HH}$=7.8 Hz, 2H), 5.78 (br. s, 1H, OH), 1.92 (s, 3H, CH$_3$).

b) 1,1-Bis(6-bromo-2-pyridyl)-1-fluoroethane

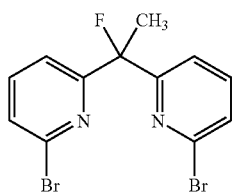 [SMILES: CC(F)(c1cccc(Br)n1)c1cccc(Br)n1]

117.3 ml (888 mmol) of DAST were added dropwise over the course of 30 min. to a solution, cooled to 10° C., of 105.9 g (296 mmol) of 1,1-bis(6-bromo-2-pyridyl)ethan-1-ol in 1500 ml of chloroform at such a rate that the temperature did not exceed 20° C. The reaction mixture was stirred at 20° C. for 1 h and then hydrolysed dropwise with 500 ml of ice-water (care: highly exothermic reaction) with ice cooling and subsequently with 1000 ml of aqueous 3M NaOH. The organic phase was separated off, the aqueous phase was extracted twice with 100 ml of chloroform, and the combined organic phases were washed once with 500 ml of water and dried over calcium chloride. After the desiccant had been filtered off, the brown organic phase was concentrated to 200 ml and filtered through a silica-gel column. The yellow solution obtained in this way was evaporated to dryness, and the yellow, viscous oil remaining was recrystallised from 200 ml of n-heptane, giving 78.6 g (218 mmol) of the product, corresponding to a yield of 73.7%, in the form of colourless crystal needles—purity according to $^1$H-NMR>99.0%.

$^1$H-NMR (CDCl$_3$): δ [ppm]=7.56 (dd, $^3J_{HH}$=7.8 Hz, $^3J_{HH'}$=7.8 Hz, 2H), 7.50 (d, $^3J_{HH}$=7.8 Hz, 2H), 7.34 (d, $^3J_{HH}$=7.8 Hz, 2H), 2.15 (d, $^3J_{HF}$=23.4 Hz, 3H, CH$_3$).

c) 1,1-Bis(6-phenyl-2-pyridyl)-1-fluoroethane

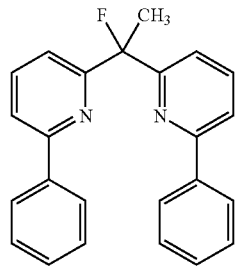 [SMILES: CC(F)(c1cccc(-c2ccccc2)n1)c1cccc(-c2ccccc2)n1]

600 µl (2.6 mmol) of tri-tert-butylphosphine and 449 mg (2.0 mmol) of palladium(II) acetate were added to a degassed suspension of 18.0 g (50 mmol) of 1,1-bis(6-bromo-2-pyridyl)-1-fluoroethane, 24.4 g (200 mmol) of benzeneboronic acid and 19.2 g (330 mmol) of potassium fluoride in 350 ml of THF, and the mixture was heated under reflux for 3 h with stirring. After cooling, the THF was removed under reduced pressure, and the residue was taken up in 500 ml of dichloromethane and washed three times with 300 ml of water. After drying over magnesium sulfate, filtration through silica gel and stripping-off of the solvent, the yellow oil remaining was recrystallised three times from ethanol, giving 15.7 g (44 mmol) of the product, corresponding to a yield of 88.6%, in the form of colourless crystal needles—purity according to $^1$H-NMR>99%.

$^1$H-NMR (CDCl$_3$): δ [ppm]=8.04 (d, $^3J_{HH}$=7.7 Hz, 4H), 7.72 (dd, $^3J_{HH}$=7.8 Hz, $^3J_{HH'}$=7.8 Hz, 2H), 7.63 (d, $^3J_{HH}$=7.8 Hz, 2H), 7.50 (d, $^3J_{HH}$=7.8 Hz, 2H), 7.44-7.35 (m, 6H), 2.35 (d, $^3J_{HF}$=23.4 Hz, 3H, CH$_3$).

Complex Synthesis

Example 1

[1,1-Bis(6-phenyl-2-pyridinato-N,C$^2$)-1-fluoroethane]platinum(II)

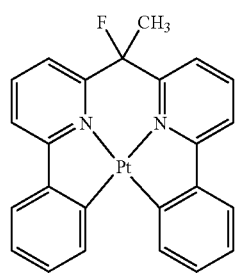

A solution of 1.063 g (3.0 mmol) of 1,1-bis(6-phenyl-2-pyridyl)-1-fluoroethane and 1.144 g (3.0 mmol) of cis-dimethyl-di(η$^1$-S-dimethylsulfoxidyl)platinum(II) in 15 ml of toluene was stirred at 90° C. for 3 h. After cooling to room temperature, 30 ml of diethyl ether were added to the yellow suspension, and the yellow, microcrystalline product was filtered off with suction and washed three times with 10 ml of diethyl ether each time. Drying under reduced pressure gave 1.544 g (2.8 mmol), corresponding to a yield of 94.0%, having a purity>99.5% (HPLC).

MS (FAB): m/e=347 (M+).

The invention claimed is:
1. A compound of the Structure 1

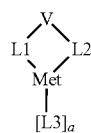

Structure 1 wherein Structure 1 contains a metal Met, coordinated to a tetradentate chelating ligand Lig of Structure 2

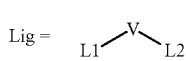

Structure 2 where V is a $CR_2$

R is, identically or differently on each occurrence, H, F, Cl, Br, I, $NO_2$, CN, a straight-chain, branched or cyclic alkyl or alkoxy group having 1 to 20 C atoms or an aryl, aryloxy or heteroaryl group having up to 14 C atoms;

$R^1$ is, identically or differently on each occurrence, H or an aliphatic or aromatic hydrocarbon radical having 1 to 20 C atoms;

V connects the two ligand moieties L1 and L2, which may be identical or different on each occurrence, covalently to one another, and where the two ligand moieties L1 and L2 satisfy Structure 3

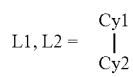

Structure 3

Cy1 is, identically or differently on each occurrence, a substituted or unsubstituted aromatic heterocyclic ring having 6 ring atoms, containing only one N atom which is bonded ionically, covalently or coordinatively to the metal via a ring atom, Cy2 is, identically or differently on each occurrence, a substituted or unsubstituted aromatic homocyclic ring having 6 ring atoms, which is bonded ionically, covalently or coordinatively to the metal via a ring atom; and Cy1 is not identical to Cy2 and one of the two rings bonds via a metal-carbon bond and the other via nitrogen, and Cy1 and Cy2 are linked to one another via substituents and thus define a polycyclic, aliphatic or aromatic ring system wherein Cy1 and Cy2 can be optionally substituted by $R^1$, and where a is 0.

2. The compound according to claim 1, wherein the compound is electrically neutral.

3. The compound according to claim 1, wherein L1 =L2.

4. The compound according to claim 1, wherein the symbol Met is Be, Mg, Pt or Zn.

5. The compound according to claim 4, wherein the symbol Met is Pt.

6. The compound according to claim 1, wherein the symbol Met is Rh or Ir.

7. The compound according to claim 1, wherein the symbol R=H, F, Cl, Br, I, CN, a straight-chain, branched or cyclic alkyl or alkoxy group having 1 to 6 C atoms or an aryl or heteroaryl group having 3 to 10 C atoms, which may be substituted by one or more non-aromatic radicals R, where a plurality of substituents R, may together in turn define a further mono- or polycyclic ring system.

8. The compound according to claim 1, wherein the compound has a purity (determined by $^1$H-NMR and/or HPLC) that is greater than 99%.

9. A conjugated, partially conjugated and/or non-conjugated polymer or dendrimer comprising one or more compounds of Structure 1 as claimed in claim 1.

10. The polymer or dendrimer according to claim 9, wherein at least one radical R represents a bond to the polymer or dendrimer.

11. The polymer according to claim 10, wherein the polymer is a polyfluorene, polyspirobifluorene, poly-para-phenylene, polydihydrophenanthrene, polyindenofluorene, polycarbazole, polythiophene, polyketone, polyvinylcarbazole or copolymers which have a plurality of the units mentioned here.

12. An electronic device comprising at least the polymer or a dendrimer according to claim 9.

13. The electronic device according to claim 12 wherein the device is an organic light-emitting diode (OLED), an organic integrated circuit (O-IC), an organic field-effect transistor (OFET), an organic thin-film transistor (OTFT), an organic solar cell (O-SC) or an organic laser diode (O-laser).

14. An electronic device comprising at least one compound according to claim 1.

15. The compound as claimed in claim 1, wherein

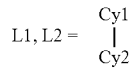

1.1 and 1.2 = wherein the ring 1 is bonded ionically, covalently or coordinatively to the metal via a ring N atom, and the ring 2 is is bonded ionically, covalently or coordinatively to the metal via a ring atom, rings 1 and 2 are linked to one another via substituents and thus define a polycyclic, aliphatic or aromatic ring system wherein rings 1 and 2 can be optionally substituted by $R^1$.

16. The compound as claimed in claim 1, wherein Met is Ir, Pd, Pt, Ag or Au.

17. The compound as claimed in claim 1, wherein Met is Pt.

18. The electronic device as claimed in claim 13, wherein the device is an organic light emitting device and wherein Met is Pt.

* * * * *